(12) United States Patent
Kapadia

(10) Patent No.: US 8,019,404 B2
(45) Date of Patent: Sep. 13, 2011

(54) APPARATUS AND METHOD FOR TARGETING A BODY TISSUE

(75) Inventor: Samir Kapadia, Chagrin Falls, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1012 days.

(21) Appl. No.: 11/867,774

(22) Filed: Oct. 5, 2007

(65) Prior Publication Data

US 2008/0249397 A1    Oct. 9, 2008

Related U.S. Application Data

(60) Provisional application No. 60/850,147, filed on Oct. 6, 2006.

(51) Int. Cl.
*A61M 25/00* (2006.01)
(52) U.S. Cl. ........ 600/433; 600/434; 600/435; 600/407; 600/424
(58) Field of Classification Search .................. 600/407, 600/410, 437, 443, 424, 439, 433–435
See application file for complete search history.

(56) References Cited

U.S. PATENT DOCUMENTS

| | | | |
|---|---|---|---|
| 5,171,228 A | 12/1992 | McDonald | |
| 5,279,583 A | 1/1994 | Shober, Jr. et al. | |
| 5,391,199 A | 2/1995 | Ben-Haim | |
| 5,487,758 A | 1/1996 | Hoegnelid et al. | |
| 6,254,586 B1 | 7/2001 | Mann et al. | |
| 6,260,552 B1 | 7/2001 | Mortier et al. | |
| 6,332,089 B1 | 12/2001 | Acker et al. | |
| 6,337,995 B1 | 1/2002 | Mower | |
| 6,622,730 B2 | 9/2003 | Ekvall et al. | |
| 6,650,923 B1 | 11/2003 | Lesh et al. | |
| 6,709,382 B1 | 3/2004 | Horner | |
| 6,740,076 B2 | 5/2004 | Hoben et al. | |
| 6,945,978 B1 | 9/2005 | Hyde | |
| 6,974,436 B1 | 12/2005 | Aboul-Hosn et al. | |
| 6,994,093 B2 | 2/2006 | Murphy et al. | |
| 6,994,094 B2 | 2/2006 | Schwartz | |
| 2002/0107445 A1 | 8/2002 | Govari | |
| 2003/0018246 A1 | 1/2003 | Govari et al. | |

(Continued)

FOREIGN PATENT DOCUMENTS

EP    0 531 081 A1    3/1993

(Continued)

*Primary Examiner* — Brian Casler
*Assistant Examiner* — Joel M Lamprecht
(74) *Attorney, Agent, or Firm* — Tarolli, Sundheim, Covell & Tummino LLP

(57) ABSTRACT

An apparatus for targeting a desired target site on a body tissue that separates a first body cavity from a second body cavity of a patient includes a catheter having a longitudinally extending catheter lumen and adapted to provide access to the first body cavity. A framing member has a collapsed condition in which the framing member is adapted for insertion into the first body cavity through the catheter lumen and an expanded condition in which the framing member is adapted for placement within the first body cavity. The framing member has a framing member body. At least one target point is carried by the framing member and is adapted for placement adjacent the desired target site. At least one target wire is attached to at least one target point. At least a portion of the target wire extends through the catheter lumen. The target wire is substantially spaced apart from the framing member body. A method of using the apparatus is also described.

26 Claims, 11 Drawing Sheets

U.S. PATENT DOCUMENTS

| | | | |
|---|---|---|---|
| 2003/0083742 A1 | 5/2003 | Spence et al. | |
| 2003/0163153 A1 | 8/2003 | Scheib | |
| 2003/0192561 A1 | 10/2003 | Murphy et al. | |
| 2004/0019447 A1 | 1/2004 | Shachar | |
| 2004/0158143 A1* | 8/2004 | Flaherty et al. | 600/407 |
| 2004/0220471 A1 | 11/2004 | Schwartz | |
| 2004/0243122 A1 | 12/2004 | Auth et al. | |
| 2005/0075723 A1 | 4/2005 | Schroeder et al. | |
| 2005/0149097 A1 | 7/2005 | Regnell et al. | |
| 2005/0154250 A1 | 7/2005 | Aboul-Hosn et al. | |
| 2005/0228452 A1 | 10/2005 | Mourlas et al. | |
| 2005/0257796 A1 | 11/2005 | Ellis et al. | |
| 2006/0025800 A1 | 2/2006 | Suresh | |

FOREIGN PATENT DOCUMENTS

| | | |
|---|---|---|
| WO | WO 96/05768 A1 | 2/1996 |
| WO | WO-99/42047 A1 | 8/1999 |
| WO | WO 03/028558 A2 | 4/2003 |
| WO | WO 03/028558 C1 | 4/2003 |
| WO | WO 2004/110307 A2 | 12/2004 |
| WO | WO 2004/110307 A3 | 12/2004 |
| WO | WO 2005/007036 A1 | 1/2005 |
| WO | WO 2005/055849 A1 | 6/2005 |
| WO | WO 2005/072627 A1 | 8/2005 |
| WO | WO 2005/113419 A2 | 12/2005 |

* cited by examiner

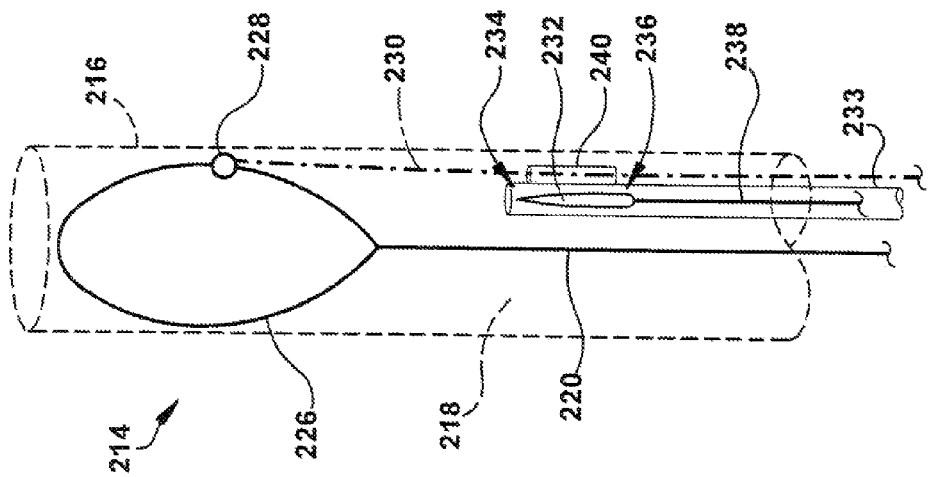
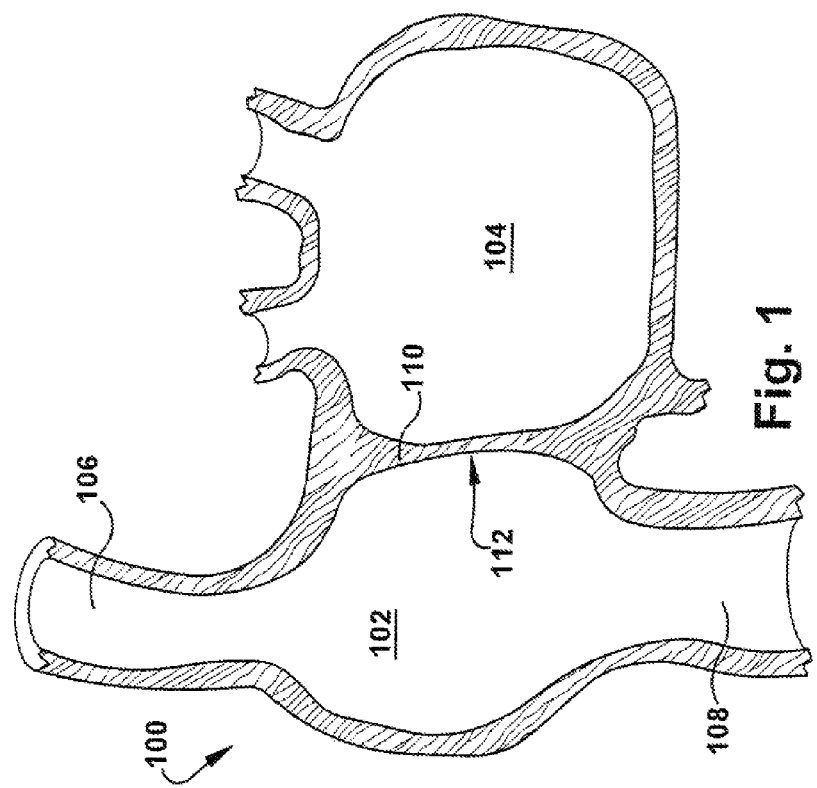

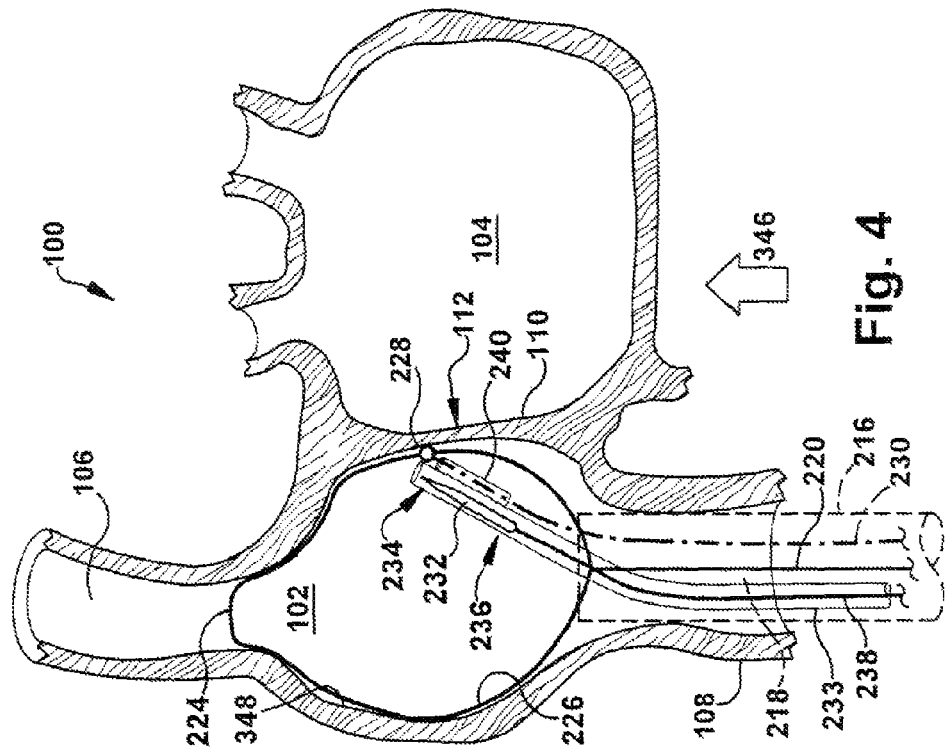
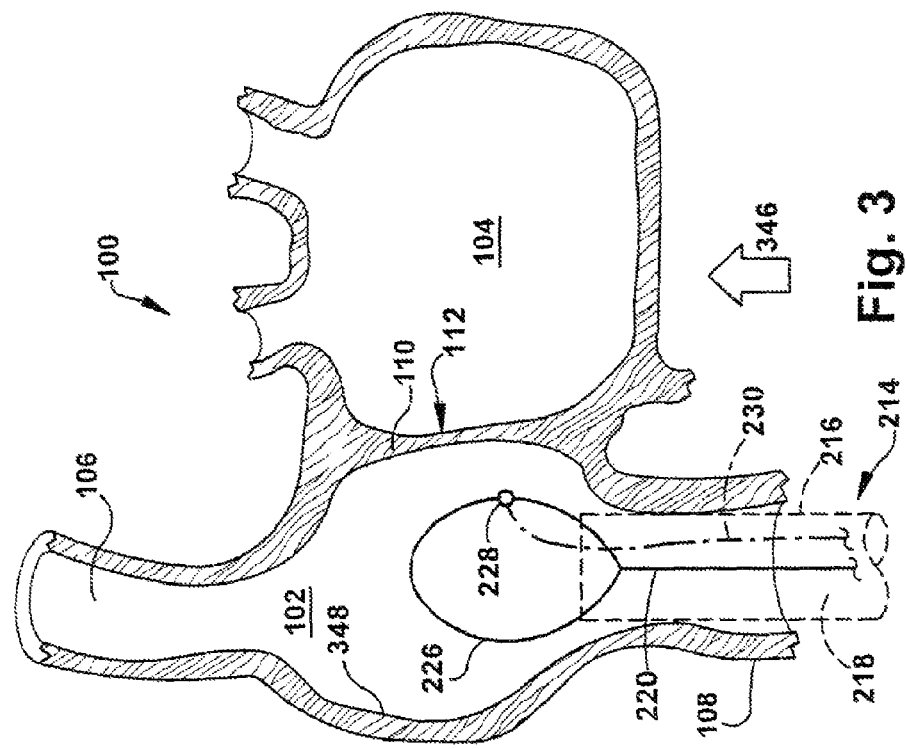

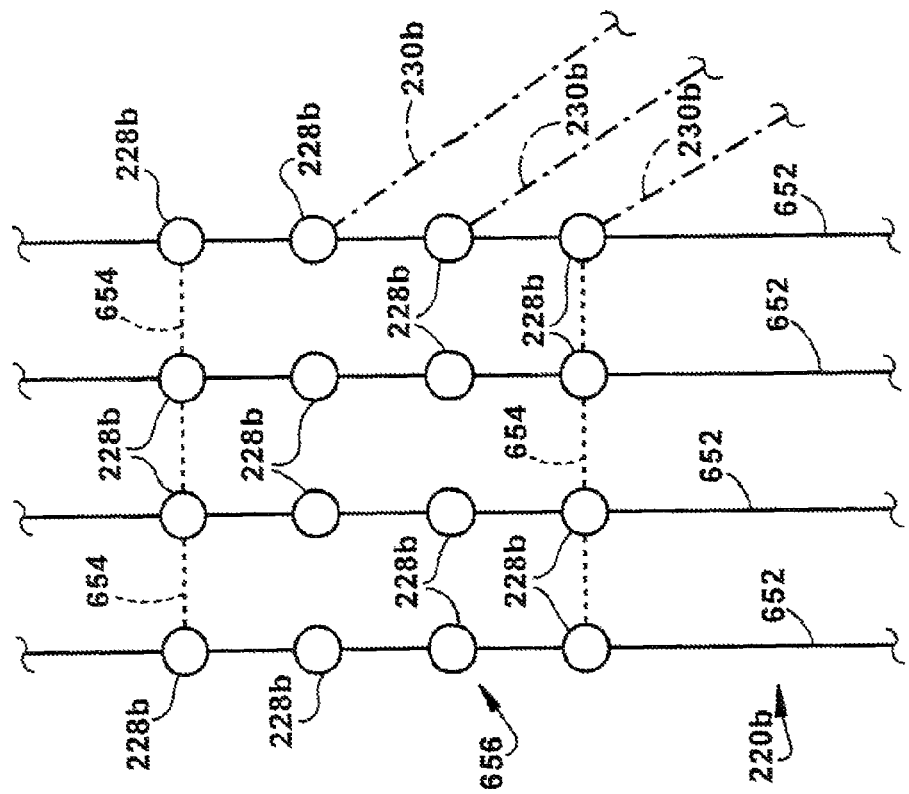
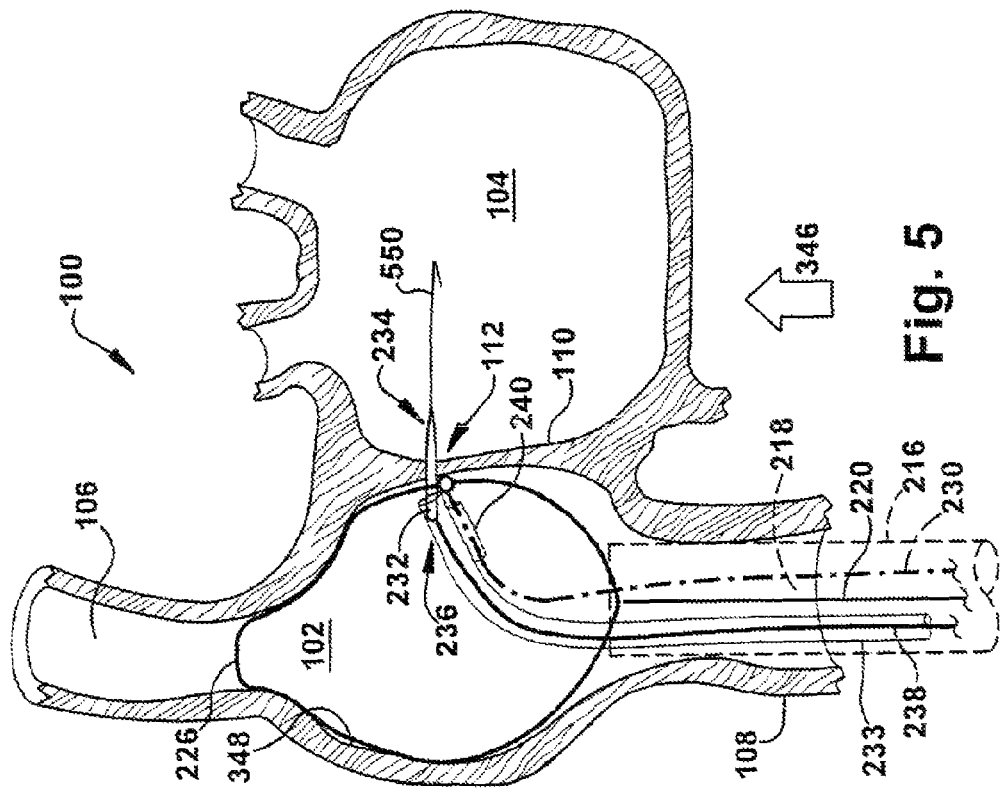

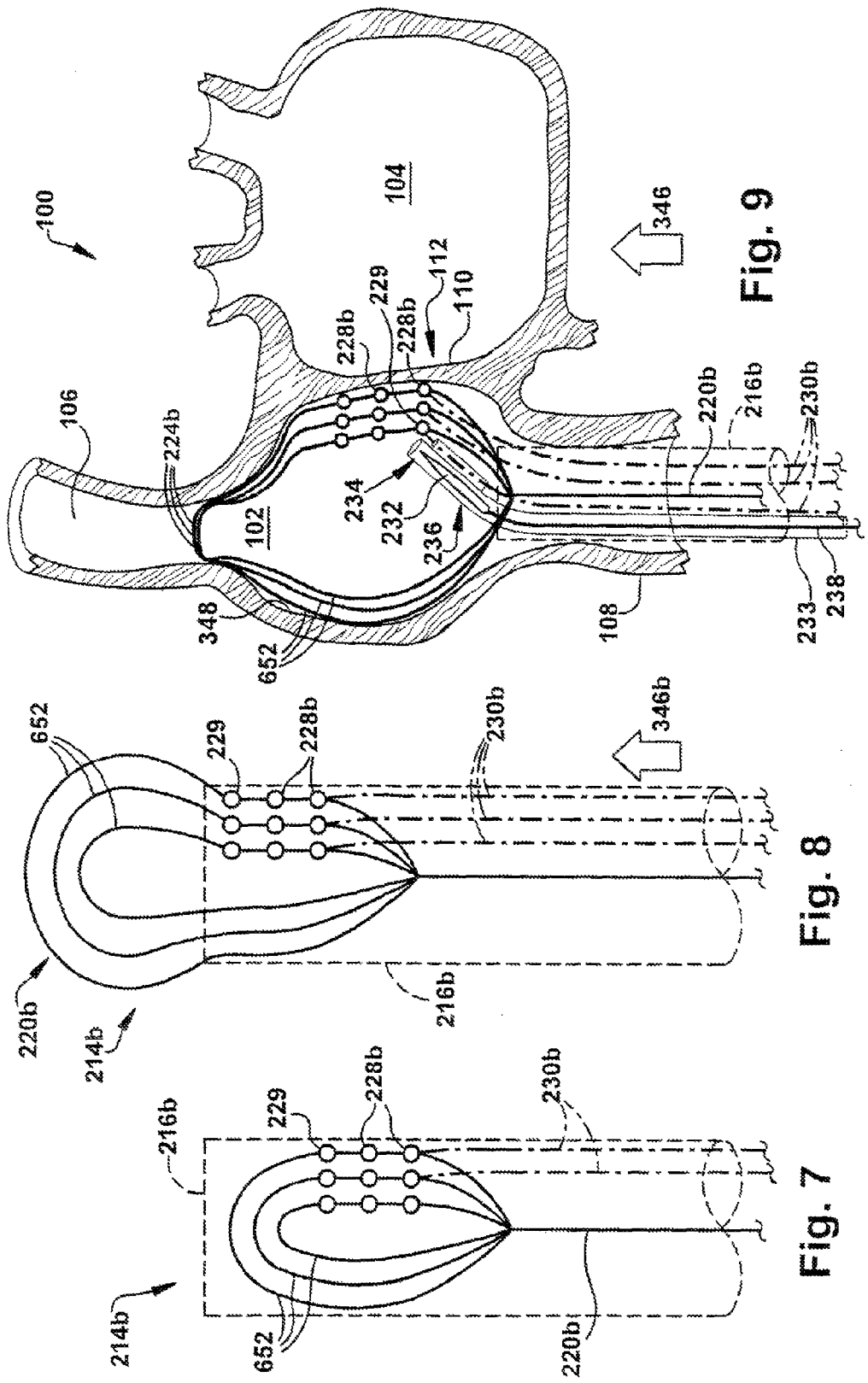

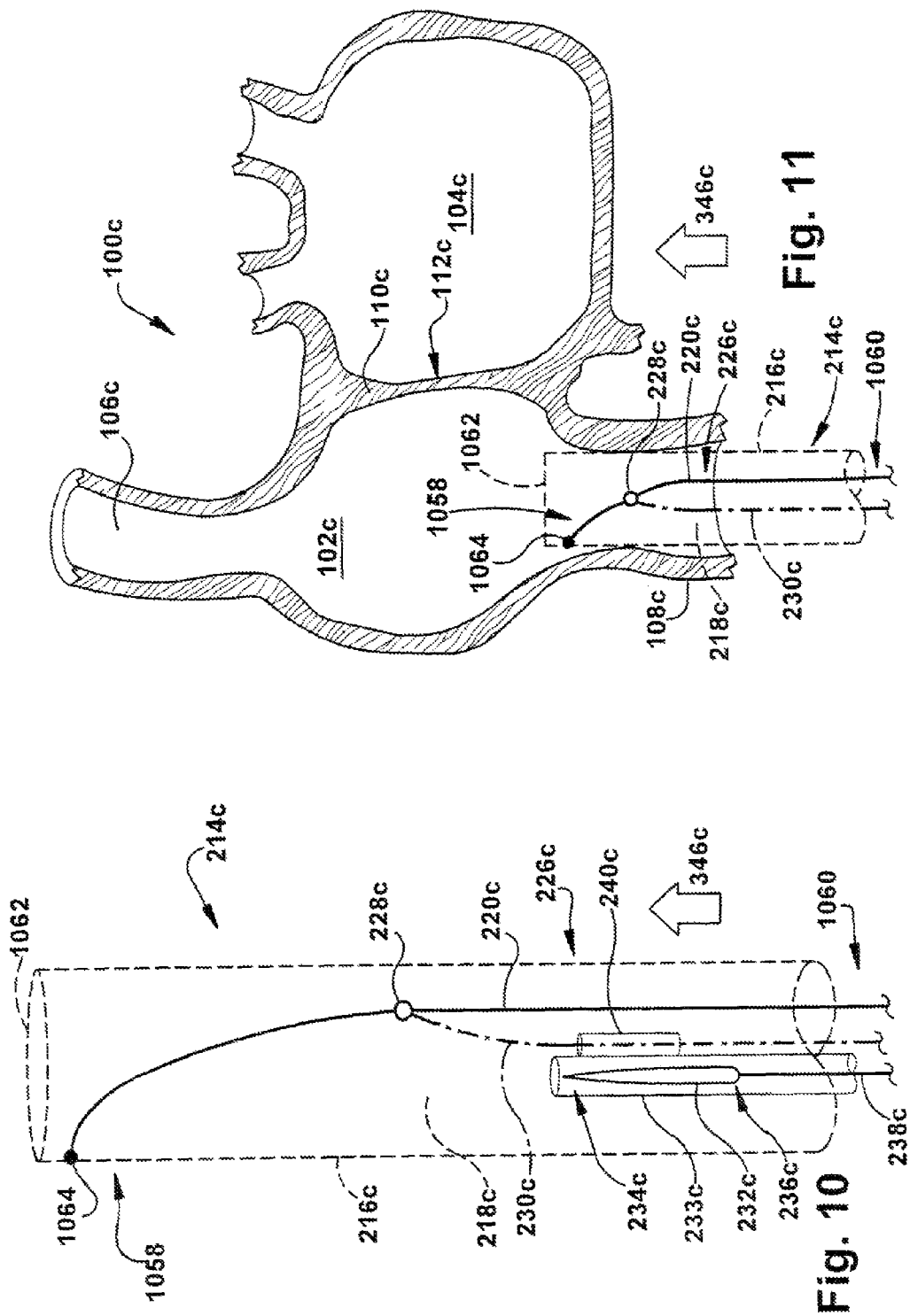

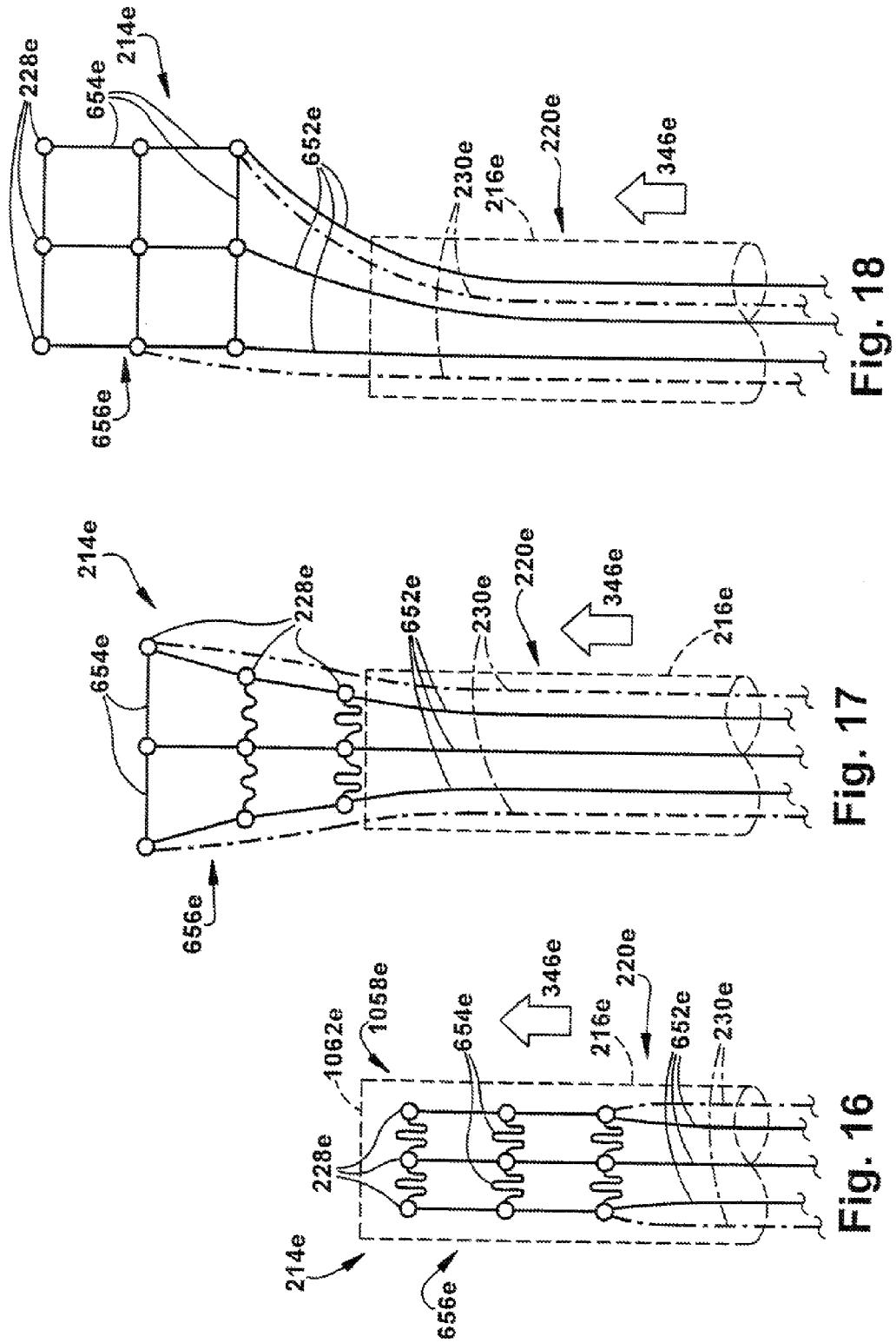

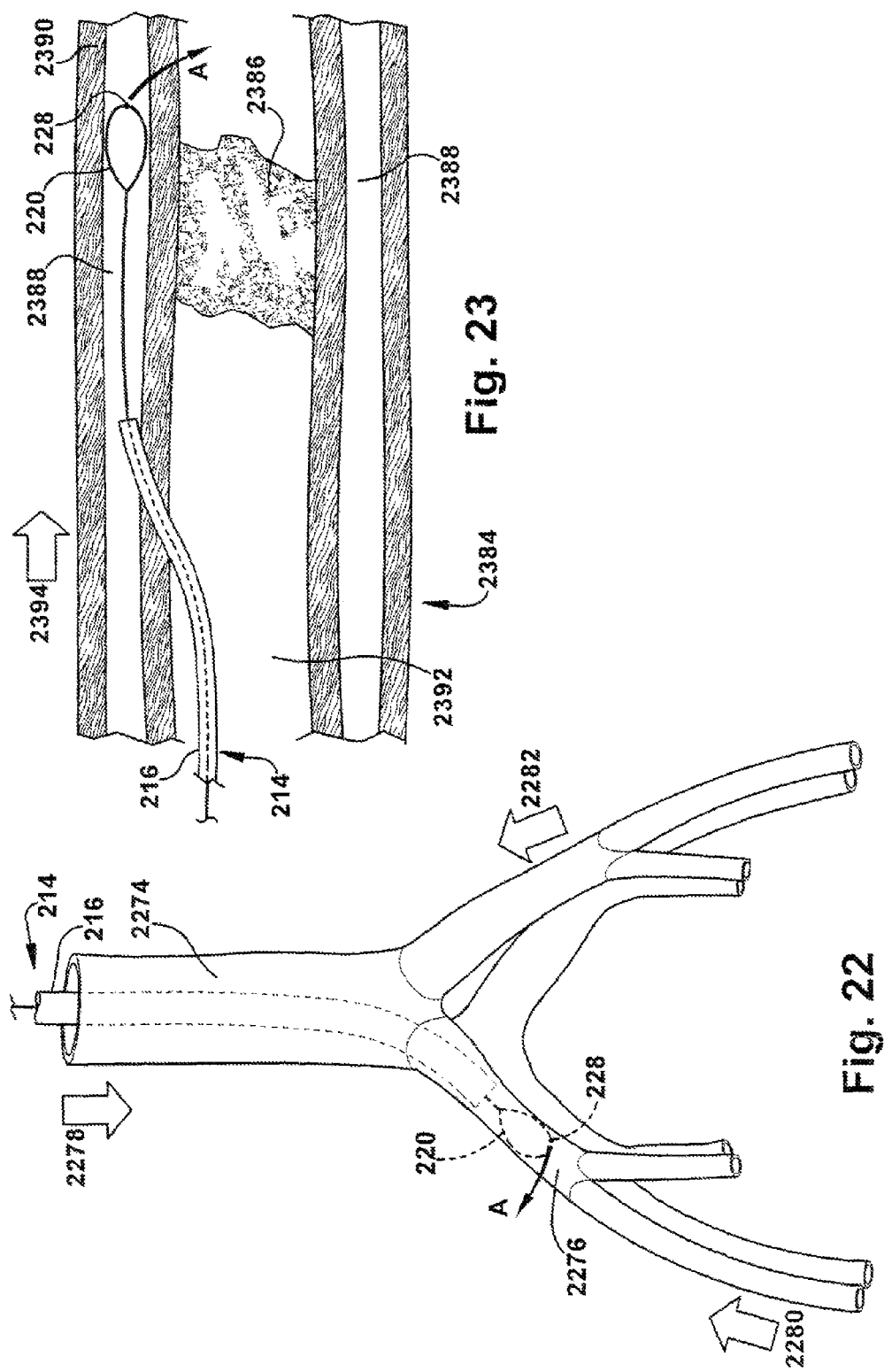

APPARATUS AND METHOD FOR TARGETING A BODY TISSUE

RELATED APPLICATION

This application claims priority from U.S. Provisional Patent Application Ser. No. 60/850,147, filed Oct. 6, 2006, the subject matter of which is incorporated herein by reference.

TECHNICAL FIELD

The present invention relates to an apparatus and method for targeting a body tissue and, more particularly, to an apparatus and method for targeting a desired target site on the body tissue.

BACKGROUND OF THE INVENTION

The typical human heart 100, a portion of which is shown in FIG. 1, includes a right ventricle, a right atrium 102, a left ventricle, and a left atrium 104. The right atrium 102 is in fluid communication with the superior vena cava 106 and the inferior vena cava 108. A tricuspid valve separates the right atrium 102 from the right ventricle. On the interatrial septum 110, which is the wall separating the right atrium 102 from the left atrium 104, is the fossa ovalis 112, a thin-walled, recessed area. In the heart of a fetus, the fossa ovalis 112 is open (patent foramen), permitting fetal blood to flow between the right and left atria 102 and 104, bypassing the fetal lungs in favor of the placental blood flow. In most individuals, this opening closes after birth.

A wide variety of diagnostic and therapeutic procedures have been developed in which a catheter is transluminally advanced into various chambers and across valves of the heart. The most difficult chamber of the heart to access with a catheter is the left atrium 104. Access to the left atrium 104 through the pulmonary artery is not possible. Approaches from the left ventricle are difficult, may cause arrhythmias, and may present difficulty in obtaining stable catheter positioning. Accordingly, the presently preferred method of accessing the left atrium 104 is through a transseptal approach, achieved by catheterization of the right atrium 102 with subsequent penetration of the interatrial septum 110. The reduced wall thickness and location of the fossa ovalis 112 make it a useful access point for a transseptal access puncture. The current methods of puncturing involve accessing the septum from the inferior vena cava 108. There is no device currently available that allows safe puncture from the superior vena cave 106.

A variety of risks are attendant to transseptal catheterization, in addition to the risks associated with normal heart catheterization. The primary additional risk is associated with inaccurate identification and localization of the interatrial septum 110 and the fossa ovalis 112 in particular. Improper placement of the catheter tip prior to the transseptal puncture presents the risk of puncture of tissue other than the interatrial septum 110, such as the aorta and/or the posterior wall of the right or left atrium 102 or 104. For this reason, catheterization is often accompanied by fluoroscopy or other visualizing techniques to assist in properly locating the catheter tip in relation to the septum 110.

The objectives of left atrial access can be either diagnostic or therapeutic. One diagnostic use is pressure measurement in the left atrium 104. In the setting of an obstructed mitral valve (mitral stenosis), left atrial access allows a determination of the pressure difference between the left atrium 104 and left ventricle. Left atrial access also allows entry into the left ventricle through the mitral valve. This is desirable when a mechanical aortic valve is in place. The advent of aortic valve replacement with mechanical artificial valves, and the increase in the aged population and growing longevity of that population subsequent to aortic valve replacement, brings a greater need to evaluate the late stage functionality of such artificial valves.

Diagnostic measurement of the left ventricular pressures is, therefore, desirable to allow evaluation of mechanical artificial aortic valves post-replacement. Crossing these mechanical artificial valves retrograde from the aorta may be nonoptimal; therefore, access to the left ventricle by an antegrade route using a transseptal puncture is generally the preferred approach. Once a catheter has been placed in the left atrium 104 using the transseptal approach, access to the left ventricle can be gained by advancing catheters across the mitral valve.

Many diagnostic indications exist for left atrial pressure measurements in addition to evaluating the functionality of artificial mitral valves. Other diagnostic indications for accessing the left ventricle via the antegrade transseptal approach include aortic stenosis, when a cardiologist is unable to pass a catheter retrograde into the left ventricle, and some disease states where the antegrade approach is considered preferable, such as subaortic obstruction.

Presently, the therapeutic objectives of left atrial access are primarily two-fold. The first is mitral valvuloplasty which represents an alternative to surgical procedures to relieve obstruction of the mitral valve. The second main therapeutic objective is for electrophysiological intervention in the left atrium 104 via catheter ablation. Catheter ablation involves the placement of energy, typically radio frequency (RF) from an electrode, through a catheter into various areas of the heart 100 to eradicate inappropriate electrical pathways affecting the heart function. When these locations are in the left atrium 104, the catheter through which the RF electrode is placed typically is itself placed into the left atrium 104 with transseptal catheterization. More recently, therapeutic treatment of the left atrial appendage to reduce the risk of embolic stroke has also been proposed.

In addition to the above, left atrium 104 access may be desirable for pulmonary vein isolation, atrial appendage closure, patent foramen ovalis closure, and aortic valve replacement or valvuloplasty. Despite clinical acceptance of a wide variety of procedures which require access to the left atrium 104, however, significant room for improvement remains in the actual access technique. For example, the step of locating an appropriate site on the interatrial septum 110, such as the fossa ovalis 112, is highly technique-dependent and can be inaccurate. Such inaccuracy may increase procedure time and/or create a risk that the needle will pierce a heart structure in an unnecessary and potentially undesirable location. Another problem is that the needle may slip while advancing toward the interatrial septum 110, resulting in an inadvertent puncture into surrounding structures within/defining the right atrium 102 before the needle even reaches the interatrial septum 110. This type of undesired puncture is particularly a risk when the left atrium 104 is large and causes the interatrial septum 110 to bulge into the right atrium 102.

In addition to the example of accessing the left atrium 104 through the interatrial septum 110, there are other occasions when it may be desirable to access a body cavity from a nearby hollow structure (vascular or otherwise) which is easier to access. Broadly, "inside-out" access to a number of different body structures could be useful in many different surgical situations. For example, a surgeon may wish to provide a cannula in the heart 100, place a conduit in an artery or vein, or to connect two adjacent body cavities by puncturing from one to the other and placing a conduit between the cavities.

Moreover, and more broadly, there are many reasons for a surgeon to desire precise location of a target site within the body, whether or not the target site is to be punctured.

SUMMARY OF THE INVENTION

In an embodiment of the present invention, an apparatus for targeting a desired target site on a body tissue that separates a first body cavity from a second body cavity of a patient is described. The apparatus includes a catheter having a longitudinally extending catheter lumen and adapted to provide access to the first body cavity. A framing member has a collapsed condition in which the framing member is adapted for insertion into the first body cavity through the catheter lumen and an expanded condition in which the framing member is adapted for placement within the first body cavity. At least one target point is carried by the framing member and is adapted for placement adjacent the body tissue to indicate the desired target site.

In an embodiment of the present invention, a method for puncturing a body tissue of a patient at a desired target site is described. A catheter having a longitudinally extending catheter lumen is inserted into the patient. The catheter is advanced into a first body cavity of the patient. A framing member carrying at least one target point is provided. The target point is adapted for placement adjacent the body tissue to indicate the desired target site. The framing member is inserted in a collapsed condition into the first body cavity through the catheter lumen. The framing member is expanded into an expanded condition within the first body cavity. The target point is positioned adjacent the body tissue. A puncture needle is inserted into the first body cavity through the catheter lumen. The puncture needle is guided to the target point. The body tissue is punctured with the puncture needle at the desired target site.

BRIEF DESCRIPTION OF THE DRAWINGS

For a better understanding of the invention, reference may be made to the accompanying drawings, in which:

FIG. 1 is a schematic cross-sectional view of a heart, showing a first example use environment;

FIG. 2 is a side view of a first embodiment of the present invention in a first condition;

FIG. 3 is a side view of the embodiment of FIG. 2 in a second condition within a heart;

FIG. 4 is a side view of the embodiment of FIG. 2 in a third condition within a heart;

FIG. 5 is a side view of the embodiment of FIG. 2 in the third condition within a heart;

FIG. 6 is a partial side view of a second embodiment of the present invention;

FIG. 7 is a side view of the second embodiment of FIG. 6 in a first condition;

FIG. 8 is a side view of the second embodiment of FIG. 6 in a second condition;

FIG. 9 is a side view of the second embodiment of FIG. 6 in a third condition;

FIG. 10 is a side view of a third embodiment of the present invention in a first condition;

FIG. 11 is a side view of the third embodiment of FIG. 10 in the first condition within a heart;

FIG. 16 is a side view of a fifth embodiment of the present invention in a first condition;

FIG. 17 is a side view of the fifth embodiment of FIG. 16 in a second condition;

FIG. 18 is a side view of the fifth embodiment of FIG. 16 in a third condition;

FIG. 22 is a schematic view of a fifth example use environment of any embodiment of the present invention;

FIG. 23 is a schematic view of a sixth example use environment of any embodiment of the present invention.

DESCRIPTION OF EMBODIMENTS

Figure 13:
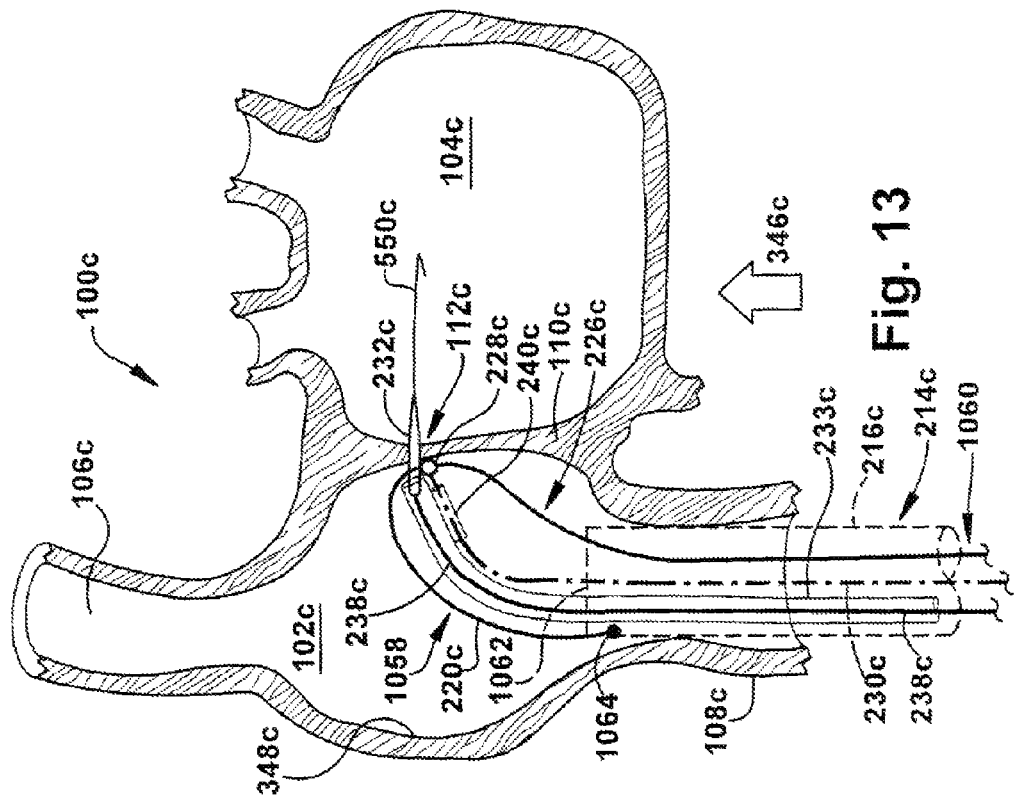
FIG. 13 is a side view of the third embodiment of FIG. 10 in a third condition within a heart.

In accordance with the present invention, FIG. 2 depicts a first embodiment of an apparatus 214 for targeting a desired target site on a body tissue. Throughout this description, the desired target site is presumed to be an interatrial septum 110 that separates a right atrium 102 from a left atrium 104 of a heart 100, but (as discussed below) may be any body tissue of a patient. Moreover, this description presumes that the desired target site is being targeted for puncture. However, the apparatus 214 could be useful in precisely locating a desired target site which is being targeted for any reason, without limitation. For example, it may be useful to target a desired target site without necessarily puncturing or otherwise altering the target site when repairing an atrial septum defect (such as a patent foramen ovalis), for dissection/location/alignment of any body structure, when repairing a perivalvular leak, for pinpointing a small branch from a blood vessel (i.e., targeting a void in a body tissue rather than a point on the body tissue), or the like. One of ordinary skill in the art could readily use the apparatus 214 for any application in which a target site is located for any reason or as a part of any procedure. However, for clarity, the below description presumes that the targeting is being accomplished preparatory to a puncture procedure.

The apparatus 214 includes a catheter 216 (shown in dashed line in FIG. 2) having a longitudinally extending catheter lumen 218 and adapted to provide access to the right atrium 102 through a blood vessel, such as the superior or inferior vena cava 106 or 108. For ease of description, the desired target site will be presumed to be the fossa ovalis 112 when the desired target site is located on an interatrial septum 110. Any desired target site, however, may be targeted by the apparatus 214.

A framing member 220 has a collapsed condition (shown as the first condition of FIG. 2) in which the framing member is adapted for insertion into the blood vessel through the catheter lumen 218. The framing member 220 shown in FIG. 2 is a loop of thin, flexible wire having a framing member body 226 and may be made of any suitable material such as, for example, a woven, drawn, or otherwise formed strand of Nitinol, stainless steel, nylon, plastic, or any other material as desired. The framing member 220 may be radiopaque, in whole or part, to facilitate positioning within the right atrium 102 as desired. The framing member 220 also has an expanded condition (shown as the second and third conditions in FIGS. 3 and 4) in which the framing member is adapted for placement within the right atrium 102. In the first embodiment, the framing member 220 is self-expanding and should be designed to have a resting configuration compatible with the right atrium 102. The framing member 220 may include a shaped feature, such as the protrusion 224, which is adapted to enter the superior vena cava 106 or another structure and facilitate rotational positioning of the framing member 220 within the right atrium 102. For example, the framing member 220 could be made from a memory alloy having the resting configuration shown in FIG. 4 but selectively compressible into the catheter 216 for delivery to the right atrium 102.

The framing member 220 carries at least one target point 228 (one shown in FIGS. 2-5). The target point 228 is adapted for placement adjacent the interatrial septum 110 to indicate the desired target site. The target point 228 may have an associated radiopaque marker (not shown) or otherwise be visible to an external imaging system or other remote detection system (not shown) when located within the patient's heart 100. The target point 228 may be affixed, as shown in FIG. 2, to the framing member body 226.

Each target point 228 may be attached to a target wire 230 (shown in dash-dot line in the Figures). The target wire 230 extends through the catheter lumen 218 between an external power source (not shown) and the target point 228. The target wire 230 may selectively provide at least one of an electrical and a mechanical signal to the target point 228 to indicate a position of the target point within the heart 100. Such indication may be made in a visual manner, and/or may be made in cooperation with an external imaging or other remote detection system.

For example, the target wire 230 could transmit a mechanical vibration to the target point 228 to cause the target point to move slightly. The external imaging system would detect such a motion and responsively indicate the location of the target point in relation to the target site on the interatrial septum 110 or another heart 100 structure. Similarly, the target wire 230 could carry an electrical current and cause the target point 228 to emit an electromagnetic signal having certain predetermined signal characteristics. The external imaging system then would detect the emitted signal and responsively indicate the location of the target point 228 within the heart 100.

A puncture needle 232 is provided. The puncture needle 232 is adapted for insertion through the catheter lumen 218 and into the right atrium 102. Optionally, and as shown in the drawings, the puncture needle 232 may be contained within a needle catheter 233. The puncture needle 232 has longitudinally spaced first and second needle ends 234 and 236, respectively, with the first needle end 234 being operative to puncture the interatrial septum 110 at the desired target site, which is optionally the fossa ovalis 112, as discussed herein. The second needle end 236 may be attached to a needle wire 238, which allows the user to remotely control the motion of the puncture needle 232 inside the needle catheter 233. The puncture needle 232 could have a hollow bore (not shown), through which a guidewire could be extended, as discussed below.

Optionally, the needle catheter 233 may be connected to the target wire 230 in a "monorail"-like manner, using a needle coupler 240. This connection allows the target wire 230 to guide the puncture needle 232 to the desired target site quickly and efficiently.

When a needle coupler 240 or other system/structure is used to guide the puncture needle 232, the target point 228 may need to be calibrated or otherwise adjusted with respect to the desired target site. One of ordinary skill in the art can readily compensate for any offset distance between the target point 228 and the actual position of the first needle end 234 which may be caused by the needle coupler 240, needle catheter 233, or other guidance structure.

The operation of the first embodiment of the present invention is depicted in the sequence of FIGS. 2-5. As discussed above, the target wire 230 and needle coupler 240 are optional, but are shown in FIGS. 2-5 for clarity of description of the first embodiment of the present invention.

First, the catheter 216 is inserted into the patient's vascular system and guided through the vascular system into or near the right atrium 102 of the heart 100, with the catheter 216 shown in FIG. 3 as entering the right atrium 102 through the inferior vena cava 108. However, the catheter 216 could instead enter the right atrium 102 through the superior vena cava 106 or in another manner. Regardless of the manner and location in which the catheter 216 is guided into position within the right atrium 102, the framing member 220 may be inserted, in the first (collapsed) condition, into the right atrium through the catheter lumen 218. The framing member 220, in the collapsed condition, need not protrude from the catheter lumen 218 within the right atrium 102, but may do so if desired.

Optionally, the catheter 216 may be inserted a relatively deep distance into the right atrium 102 or through the right atrium and into the superior vena cava 106, and the framing member 220 may be maintained at that insertion depth within the right atrium or superior vena cava. The catheter 216 may then be at least partially retracted from the right atrium 102, thus moving relative to the framing member 220 and unsheathing the framing member. This technique may be useful when a protrusion 224 or other nonuniformity of the framing member 220 is provided to mate with the superior vena cava 106. Otherwise, the catheter 216 may be maintained at a relatively shallow insertion distance into the right atrium 102, as shown in FIGS. 3-5, and the framing member 220 may then be moved into the right atrium, in an advancement direction 346, to emerge from the catheter.

The framing member 220 is then expanded into the second (expanded) condition within the right atrium 102, as shown in the sequence of FIGS. 3-4. This expansion may be done in whole or in part, and as quickly as desired, depending upon the particular application of the apparatus 214. As mentioned above, the framing member 220 of the first embodiment is self-expanding into the expanded condition and may include a protrusion 233 for locating the framing member within the right atrium 102.

As the framing member body 226 is brought into position within the right atrium 102 as desired, the framing member 220 may be manipulated to position the target point 228 adjacent the interatrial septum 110. Optionally, the target point 228 may contact the interatrial septum 110. The location of the target point 228 on the framing member 220 should be predetermined to facilitate positioning adjacent the interatrial septum 110 as desired.

Optionally, the target point 228 may be slidably fastened to, or otherwise movable with respect to, the framing member 220. In such case, the target wire 230, when present, may assist in moving the target point 228 along the framing member 220 and into the desired position adjacent the interatrial septum 110.

When the framing member 220 has been expanded into the right atrium 102 and arranged as desired to bring the target point 228 into the desired position adjacent the interatrial septum 110, at least a portion of the framing member body 226 may lie in contact with the interatrial septum. That is, the framing member 220 may contact one or more locations on, or areas of, the interatrial septum 110.

The right atrium 102 includes an internal right atrium surface 348, of which the interatrial septum 110 forms a portion. The framing member 220 may exert a positive pressure on any areas of the internal right atrium surface 348 when in the expanded condition. The framing member 220 is optionally designed to brace against areas of the internal right atrium surface 348 remote from the interatrial septum 110 in order to maintain contact between the target point 228 and the interatrial septum. For instance, the framing member 220 may be designed to be slightly larger than the internal right atrium surface 348 in one or more dimensions when in the expanded condition, in order to exert a positive pressure needed to maintain the target point 228 in a desired position.

In order to confirm that the target point 228 is located adjacent the interatrial septum 110 as desired before the surgery proceeds, the position of the target point 228 may be viewed within the right atrium 102 using an external imaging system (not shown). The position may be established and viewed passively when the target point 228 includes a radiopaque or other marker.

Alternately, an active determination of the position of the target point 228 may be made, such as by selectively providing at least one of an electrical and a mechanical signal through the target wire 230 to the target point 228. An external imaging or other remote detection system may be used to sense a position-indication motion or signal produced by the target point 228 responsive to the electrical and/or mechanical signal. The user can then review the output of the remote detection system to determine the location of the target point 228 within the right atrium 102. This position-checking process may be repeated as needed at any suitable time throughout the targeting procedure.

A puncture needle 232 may be inserted into the catheter 216, through use of a needle catheter 233, at any suitable time before or during the septal puncture procedure. The needle catheter 233 may be coupled to the target wire 230, when present, or may be guided independently, as previously discussed. For ease of description below, it is presumed that a needle coupler 240, which may be a loop of suture thread, a monorail catheter coupler, or have any other suitable structure, attaches the needle catheter 233 to the target wire 230.

The needle catheter 233 is passed through the catheter lumen 218 into the right atrium 102 and is guided to the target point 228, advancing in the advancement direction 346. As shown in FIGS. 4 and 5, this guidance may occur along the target wire 230. When the needle catheter 233 reaches the interatrial septum 110 at or adjacent the desired target site, the puncture needle 232 is moved in the advancement direction 346 relative to the needle catheter 233. This motion should be sufficient for the puncture needle 232 to puncture the interatrial septum at the desired target site and allow the first needle end to enter the left atrium 104.

Once the puncture needle 232 has passed at least partially through the interatrial septum 110, the left atrium 104 may be accessed through the puncture at the target site in any suitable manner. For example, a guidewire 550 could be advanced through the needle catheter 233, optionally following the needle wire 238, and into the left atrium 104. As shown in FIG. 5, the guidewire 550, when present, may be inserted through a hollow bore (not shown) of the puncture needle 232 and into the left atrium 104. Once the guidewire 550 is in place, the puncture needle 232 and needle wire 238, and optionally the needle catheter 233, can be removed from the catheter 216. With the guidewire 550 in place, the left atrium 104 can be accessed as desired in a known manner as the surgical procedure progresses.

The apparatus 214, or portions thereof, may be removed from the right atrium 102 if desired, by reversing all or part of the above process. The guidewire 550, particularly, may be left in place after removal of other portions of the apparatus 214 to facilitate access to the left atrium 104. Optionally, the catheter 216 may remain in position after the puncture is made to continue right and left atrium 102 and 104 access as the surgery progresses, with the framing member(s) 220, target wire(s) 230, and/or puncture needle 232 being retracted through the catheter 216 and removed from the patient. The catheter 216, guidewire 550, and any other portions of the apparatus 214 which were left in place within the patient may be removed as the surgery concludes.

FIGS. 6-9 illustrate a second embodiment of an apparatus 214b. The apparatus 214b of FIGS. 6-9 is similar to the apparatus of FIGS. 2-5 and therefore, structures of FIGS. 6-9 that are the same as or similar to those described with reference to FIGS. 2-5 have the same reference numbers with the addition of the suffix "b". Description of common elements and operation similar to those in the previously described first embodiment will not be repeated with respect to the second embodiment.

The framing member 220b of the second embodiment is made up of a plurality of framing strands 652, with each framing strand 652 being similar to the framing member 220 of the first embodiment. The framing strands 652 are optionally attached together with framing cross members 654, shown in dashed line in FIG. 6. Whether or not framing cross members 654 are provided, the framing member 220b carries a plurality of target points 229 forming a target grid 650. The target grid 650 shown in the Figures as being rectilinear. However, the target grid, like all structures described herein, could have any suitable two- or three-dimensional shape, profile, or configuration. Each target point 229 may have a corresponding target wire 230b, most of which are omitted throughout the Figures in all embodiments for clarity. Those target wires 230b shown in the Figures as examples have no particular significance distinguishing them from the omitted target wires 230b.

The framing member 220b of the second embodiment is expanded into the expanded condition much like the framing member 220 of the first embodiment, as shown in the sequence of FIGS. 7-9. The catheter 216b and framing member 220b are moved relatively, such as by movement of the framing member in the advancement direction 346b. The framing member 220b of the second embodiment is self-expanding, as shown in the sequence of FIGS. 7-9, and is designed to occupy at least a portion of the right atrium 102, as with the framing member 220 of the first embodiment.

The framing member 220b is used to help position at least a portion of the target grid 650 adjacent the interatrial septum 110b. The position of the target grid 650 within the right atrium 102b is then determined. Optionally, this is done by viewing the target grid 650 using an external imaging or other remote detection system (not shown).

For example, a target wire 230b corresponding to a test target point 229, for example, the top right target point 229 (as viewed in FIG. 7), may be used to selectively provide at least one of a mechanical and an electrical signal to that test target point 229. The resultant signal produced by the test target point 229 may then be viewed with the external imaging or other remote detection system to determine the position of that test target point 229 within the right atrium 102b. This process can be repeated as needed until the position of each target point 229 is known, either directly or through extrapolation from other, directly detected, target points 229.

Once the position of the target grid 650 is known, a closest target point 229 to a desired target site, or another target point 229 having a desired relationship with the desired target site, may be chosen. For a puncture procedure in which a target wire 230b is used to guide the needle catheter 233b, the needle coupler 240b is attached to the target wire 230b corresponding to that selected target point 229. Whether or not the needle catheter 233b is guided by the target wire 230b, the puncture needle 232b can be guided to the selected target point 229 and puncture the interatrial septum 110b at the desired target site in much the same manner as described above.

FIGS. 10-13 illustrate a third embodiment of an apparatus 214c. The apparatus 214c of FIGS. 10-13 is similar to the apparatus of FIGS. 2-5 and therefore, structures of FIGS. 10-13 that are the same as or similar to those described with reference to FIGS. 2-5 have the same reference numbers with the addition of the suffix "c". Description of common elements and operation similar to those in the previously described embodiments will not be repeated with respect to the third embodiment.

In the third embodiment of FIG. 10, the framing member 220c may be an elongated framing member having longitudinally spaced first and second framing member ends 1058 and 1060, respectively, separated by an intermediate framing member body 226c. The catheter 216c has a catheter outlet end 1062 in fluid communication with the right atrium 102c. The framing member 220c depicted in FIGS. 10-13 is a fairly stiff but elastically deformable wire, with the first framing member end 1058 anchored to the catheter 216d at an anchor point 1064 adjacent the catheter outlet end 1062. The framing member 220c does not need to be self-expanding in the third embodiment of the present invention because the expansion may be effected by outside forces acting on the framing member 220c.

The anchoring attachment may be static, such as a weld, or dynamic, such as a pivoting joint. The anchor point 1064 may be at any location on the inside or outside of the catheter 216c and may be readily chosen for a particular application of the apparatus 214c by one of ordinary skill in the art. The anchor point and/or type may be chosen to steer the framing member body 226c to expand asymmetrically, as shown in FIGS. 12-13.

Figure 12:
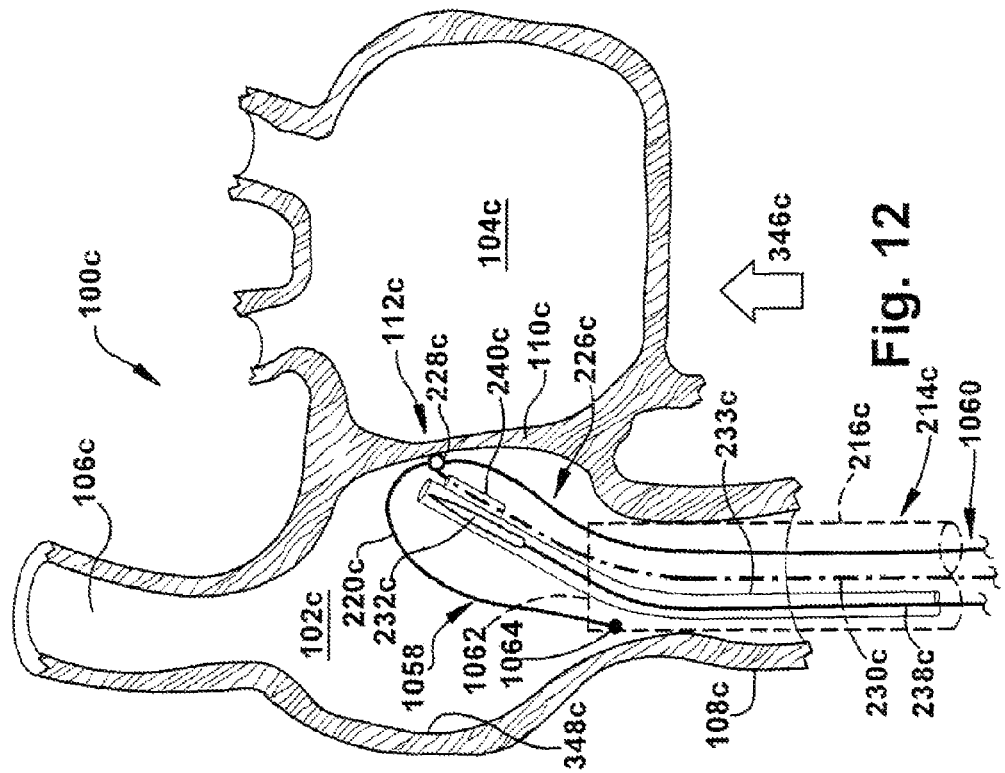
FIG. 12 is a side view of the third embodiment of FIG. 10 in a second condition within a heart.

Deployment of the apparatus 214c is shown in the sequence of FIGS. 11-13. To expand the framing member 220c into the second, expanded condition within the right atrium 102c, the second framing member end 1060 is advanced toward the right atrium, as indicated by the advancement direction arrow 346c. Since the first framing member end 1058 is affixed to the catheter 216c at the anchor point 1064, advancement of the second framing member end 1060 will cause at least a portion of the framing member body 226c to bow out into the right atrium 102c, as shown in FIGS. 12 and 13.

Once the framing member 220c has reached the expanded condition (shown as the second condition in FIG. 12), the position of the target point 228c can be checked and adjusted as needed, optionally with the assistance of a radiopaque marker or of a target wire 230c and remote detection system, as described above. The needle catheter 233c, when used in a puncture procedure, may be guided to the desired target site in any suitable manner, such as along the target wire 230c using a needle coupler 240c, as depicted in FIGS. 12 and 13. The interatrial septum 110c may then be punctured, a guidewire 550c optionally placed into the left atrium 104, and the apparatus 214c withdrawn from the heart 100c, as with the first and second embodiments described above.

Figure 14:
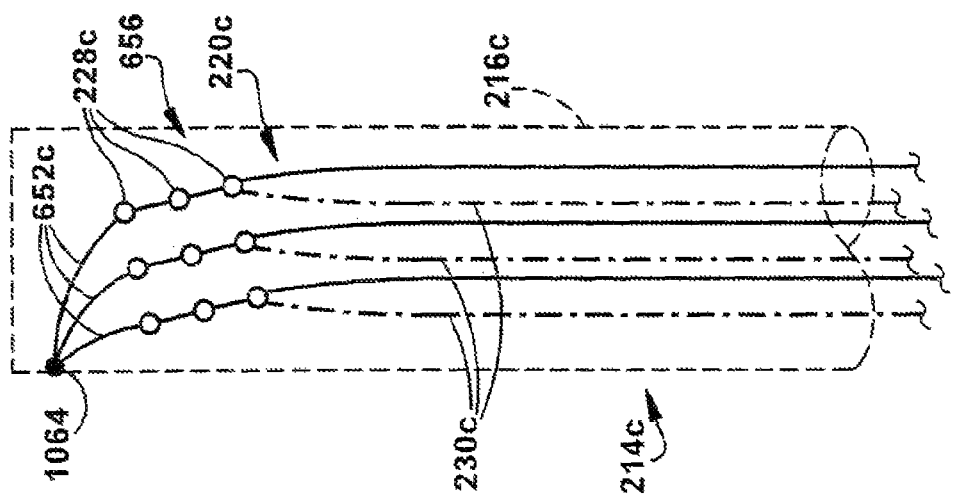
FIG. 14 is a side view of an alternate configuration of the third embodiment of the present invention in a first condition.

FIG. 14 depicts an alternate configuration of the third embodiment. The alternate configuration bears similarities to the second embodiment, in that a plurality of framing strands 652c make up the framing member 220c, and a plurality of target points 228c are arranged in a target grid 656. However, the multi-strand alternate configuration of FIG. 14 is deployed similarly to the single-strand framing member 220c previously described as the third embodiment. The framing strands 652c may be connected by framing cross members (not shown), or the apparatus 214c of the alternate configuration depicted in FIG. 14 may otherwise incorporate any suitable features from either the second or third embodiment of the present invention.

Figure 15:
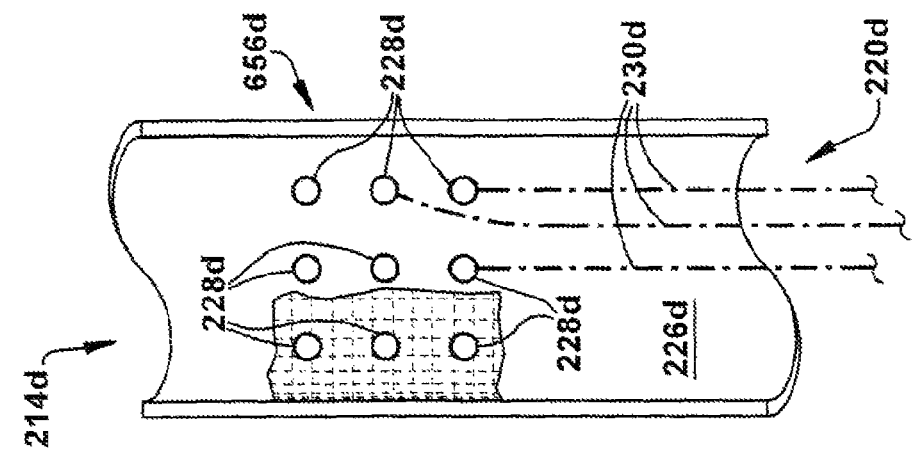
FIG. 15 is a partial side view of a fourth embodiment of the present invention.

FIG. 15 illustrates a fourth embodiment of an apparatus 214d. The apparatus 214d of FIG. 15 is similar to the apparatus of FIGS. 2-5 and therefore, structures of FIG. 15 that are the same as or similar to those described with reference to FIGS. 2-5 have the same reference numbers with the addition of the suffix "d". Description of common elements and operation similar to those in the previously described embodiments will not be repeated with respect to the fourth embodiment.

The framing member 220d of the fourth embodiment has a flat, elongated ribbon-like structure, at least for the planar framing member body 226d portion thereof. The framing member 220d may be self-expanding, but is not necessarily so. The first and second framing member ends (not shown) may be of any suitable configuration. A plurality of target points 228d are arranged in a target grid 656d on a planar surface of the framing member body 226d. Target wires 230d may connect one or more target points 228d with one or more external power sources, for ease of location of the respective target points 228d within the right atrium.

The framing member 220d may be at least partially perforated or formed from mesh, an example portion of which is shown in dotted line in FIG. 15, to allow for the puncture needle or other structures to easily extend and/or pass through the thickness of the framing member 220d.

The framing member 220d of the fourth embodiment may be deployed similarly to the framing members 220b or 220c of the previously described second or third embodiments of the present invention. That is, the planar framing member body 226d and the target grid 656d may be part of either a closed-loop framing member 220b as in the second embodiment, or an anchored framing member 220c as in the alternate configuration of the third embodiment. In either case, the framing member body 226d is positioned in the right atrium with at least a portion of the target grid 656d adjacent the interatrial septum. The target point 228d location procedure may then be carried out as described above, with the interatrial septum being punctured (if desired) and the apparatus 214d removed from the right atrium as with the other embodiments of the present invention.

FIGS. 16-18 illustrate a fifth embodiment of an apparatus 214e. The apparatus 214e of FIGS. 16-18 is similar to the apparatus of FIGS. 2-5 and therefore, structures of FIGS. 16-18 that are the same as or similar to those described with reference to FIGS. 2-5 have the same reference numbers with the addition of the suffix "e". Description of common elements and operation similar to those in the previously described embodiments will not be repeated with respect to the fifth embodiment.

The apparatus 214e of the fifth embodiment includes a framing member 220e having a plurality of framing strands 652e connected by flexible framing cross members 654e. The framing strands 652e are self-expanding and are arranged to draw the framing cross members 654e taut in the second, expanded condition. The framing member 220e is held in a compressed configuration to fit within the catheter 216e in the first, collapsed condition.

The framing member 220e supports a plurality of target points 228e in a target grid 656e. Any number of target points 228e may have an associated target wire 230e. Unlike the previously described embodiments, the target grid 656e is located at or near the first framing member end 1058e of the framing member 220e in the fifth embodiment.

To deploy the framing member 220e of the fifth embodiment, the framing member and catheter 216e are relatively moved, such as by extending the framing member in the advancement direction 346e. As depicted in the sequence of FIGS. 17-18, the framing strands 652e begin to self-expand and separate from each other as they are released from the catheter outlet end 1062e. The framing cross members 654e restrain the framing strands 652e and thereby retain the target points 228e in the target grid 656e configuration.

In FIG. 18, the framing member 220e has reached the second, expanded condition, with the target grid 656e held apart from the catheter 216e in a cantilevered manner. The framing member 220e may then be manipulated to bring the target grid 656e adjacent the interatrial septum. The framing member 220e may be bent or curved in a predetermined manner to facilitate placement of the target grid 656e as desired with respect to the interatrial septum. Optionally, the framing strands 652e are of a sufficiently stiff material to allow for positive pressure to be applied against the interatrial septum by the target grid 656e.

Once the target grid 656e is in the desired position within the right atrium 102, the target point 228e location procedure may be carried out as described above, with the interatrial septum 110 being punctured and the apparatus 214e removed from the right atrium as with the other embodiments of the present invention.

As alluded to previously, any of the first through fifth embodiments of the present invention could be used to target a desired target site on any body tissue. Additionally, the target site could be chosen for any reason or because of any characteristic; as discussed previously, locating a puncture site is only one of many possible uses for the present invention. The body tissue could separate first and second body cavities of any portion of the patient's anatomy. As used herein, "body cavity" simply means an area of the patient's body from which or to which access is desired, such access to be provided by puncturing the body tissue. The first and second body cavities in the previously described use environment are the right and left atria 102 and 104, respectively. A "body cavity" need not be a tightly enclosed or defined open volume within the body, but could be any lumen within, or space between, any body structures, no matter how minimal. For ease of description, access to or from a "body cavity" will be considered herein to also encompass access between an internal body location and the space external to the patient's body (for example, puncturing through the abdominal skin inward to or outward from the peritoneal cavity for direct access thereto through the patient's abdomen).

FIGS. 19-23 schematically depict various nonlimiting example use environments of any embodiment of the present invention, in addition to the first example use environment previously depicted and described with respect to the first through fifth embodiments. However, the apparatus 214 of the first embodiment will be shown in schematic form in these Figures, for simplicity. Additionally, operation of several embodiments of the apparatus 214 has been previously described and will not be repeated below.

Figure 19:
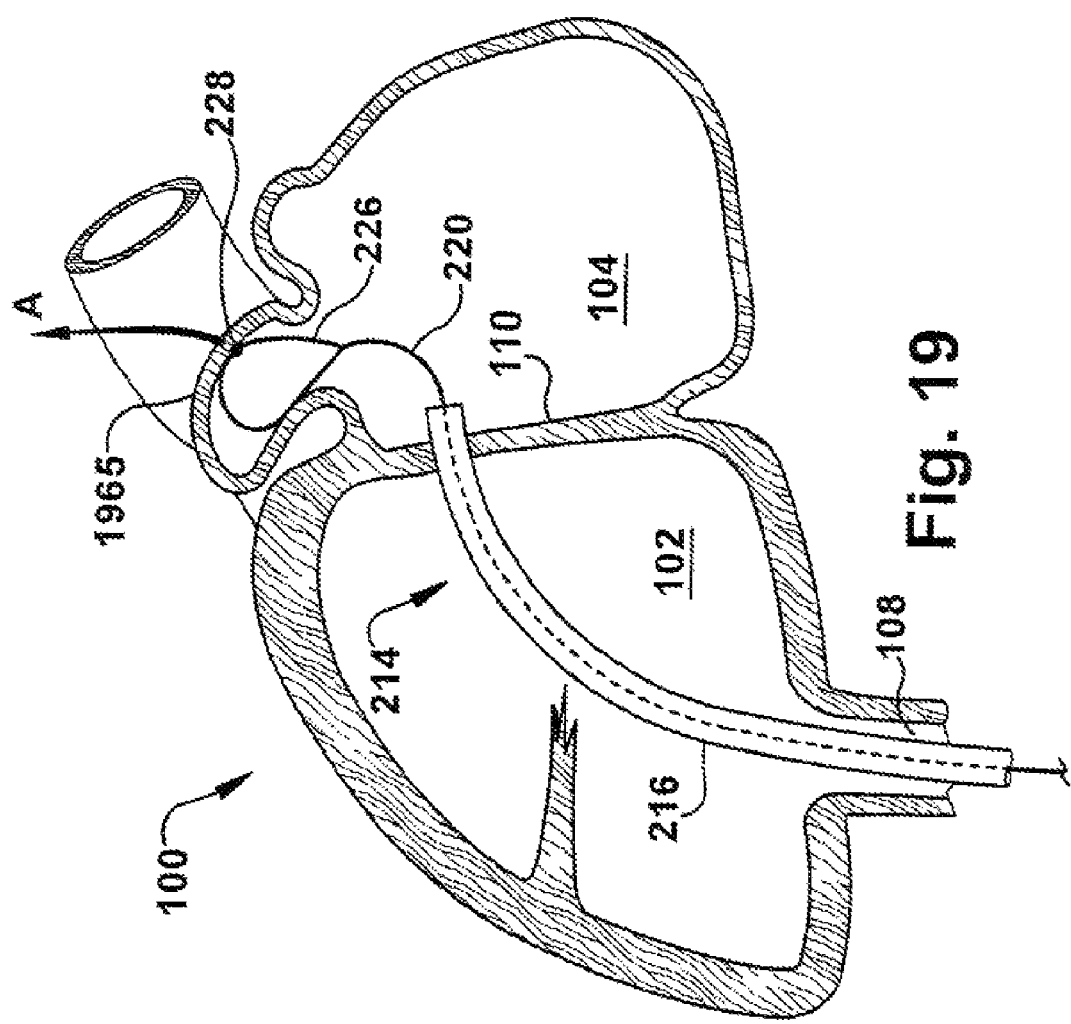
FIG. 19 is a schematic view of a second example use environment of any embodiment of the present invention.

FIG. 19 is a partial cross-sectional view of a heart 100 having right and left atria 102 and 104. In the second example use environment depicted, the catheter 216 has traveled through the inferior vena cava 108 to the right atrium 102. The apparatus 214 has already been used once to puncture through the interatrial septum 110, with the catheter 216 following the framing member 220 through the interatrial septum. However, the catheter 216 could instead be held within the right atrium 102, with only the framing member extending through the interatrial septum 110, as desired.

In the second example use environment of FIG. 19, the apparatus 214 is in a desired position on the body tissue forming a left atrial appendage 1966 of the heart 100. Arrow A depicts a possible path for a needle (not shown) to exit the left atrial appendage 1966 by a puncture at or near the target point 228, when such egress is desired. Such precise target site location within the left atrial appendage 1966 could be useful in many different surgical procedures. It is well-known that blood often clots within the left atrial appendage 1966, causing a risk of stroke, so it may be desirable, for example, to locate and/or prepare a target site for anchoring a blocking device within the left atrial appendage.

Since the left atrial appendage 1966 is not a "working tissue" of the heart 100, a puncture therethrough (and the resultant scar tissue) will not hinder ongoing operation of the heart. Accordingly, access into or out of the heart 100 may be desirably provided through the left atrial appendage 1966 wall, to avoid damaging otherwise intact structures and tissues of the heart during access. For example, the catheter 216 may be inserted into the body endovascularly, as shown in FIG. 19, and the left atrial appendage 1966 punctured (with targeting assistance from the apparatus 214). The catheter 216 could then be advanced through the left atrial appendage 1966 and through the chest cavity structures in an outward direction. The apparatus 214 could then be used to precisely target an emergence location for the catheter 216 to pass through the patient's chest wall and provide direct percutaneous access to the heart 100 without necessitating a potentially damaging and imprecise cut-down procedure from the patient's chest wall toward the heart. Thus, the patient's chest structure could be more readily navigated, and possibly preserved, during percutaneous procedures (for example, aortic or mitral valve replacements) using the apparatus 214 and the described "inside-out" technique than if the heart 100 were to be blindly accessed from the outside in, as is traditionally done. Further, chest incisions and/or exposure of the heart 100 to the ambient atmosphere, for stabilizing the cardiac structures, are avoided through use of this inside-out access.

Figure 20:
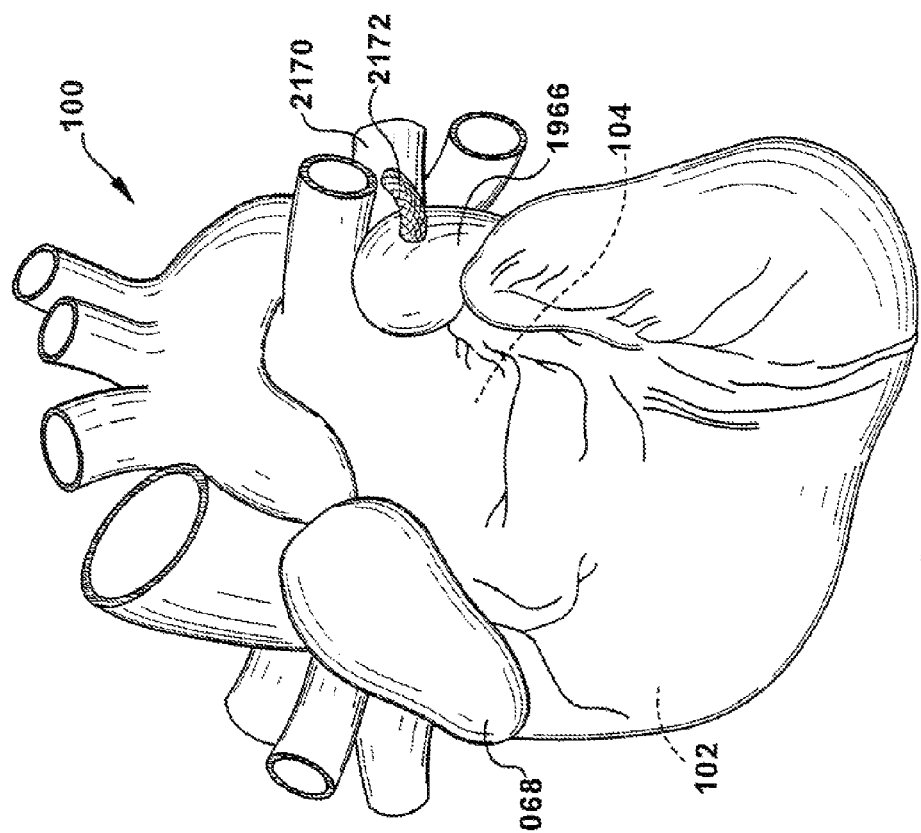
FIG. 20 is a schematic view of a third example use environment of any embodiment of the present invention.

FIG. 20 is a schematic external view of the heart 100, depicting a third example use environment of any embodiment of the present invention. The third example use environment is similar to the second example use environment, except that instead of the left atrial appendage 1966, the apparatus 214 is being used to locate a target site within a right atrial appendage 2068. The catheter 216 has previously been inserted into the right atrium 102 in any suitable manner, and the framing member 220 is depicted in FIG. 20 as being located adjacent the body tissue making up the right atrial appendage 2068 wall. The target point 228 in FIG. 20 is located adjacent an inner surface of the right atrial appendage 2068 wall, ready to guide a needle (not shown), if desired, to puncture from that location within the right atrial appendage 2068 outward from the heart 100, possibly in the direction of Arrow A. Inside-out access through the right atrial appendage 2068 in this manner may be useful, for example, in conducting surgical procedures on one or more of the tricuspid valve, pulmonary valve, or interatrial septum.

In either of the second or third example use environments, or any other use environment, the apparatus 214 can be used in the reverse orientations from those depicted. That is, the apparatus 214 can enter the patient's body from outside the heart 100 in any desired manner, and the target point 228 can be used to accurately identify a desired target site on either the left or right atrial appendage 1966 or 2068 or another portion of the heart 100, through which the interior of the heart can be accessed. Though the left and right atrial appendages 1966 and 2068 are used as examples herein, the apparatus 214 could be used at any location on the heart 100, internally or externally, to assist in providing either inward or outward access through a heart wall.

Figure 21:
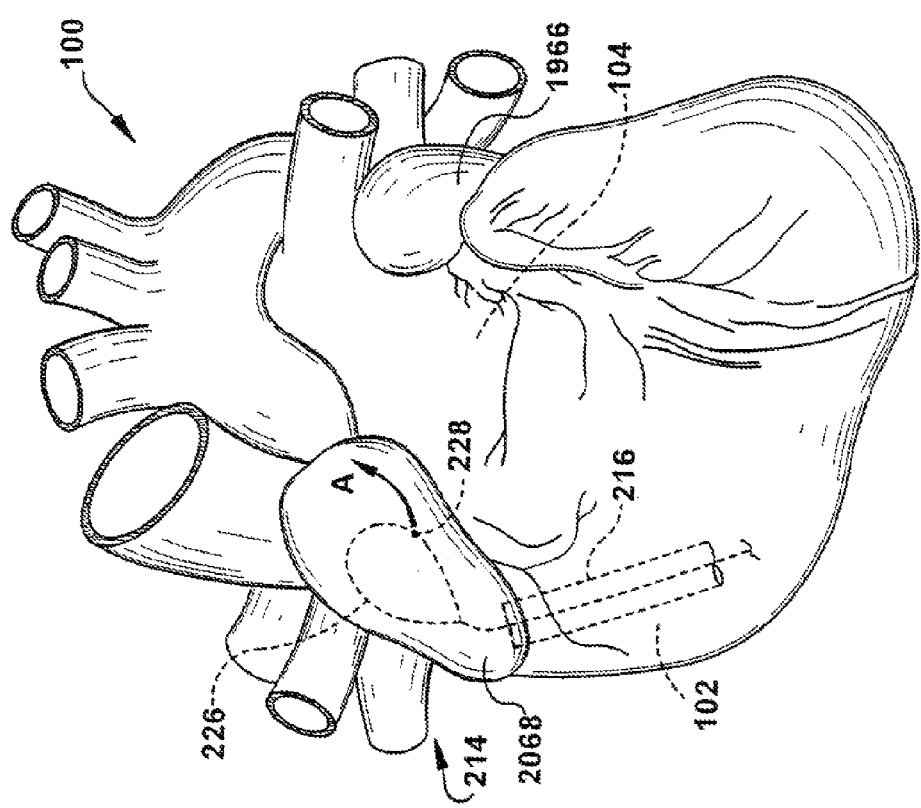
FIG. 21 is a schematic view of a fourth example use environment of any embodiment of the present invention.

A fourth example use environment of any embodiment of the present invention is depicted in FIG. 21. As previously mentioned, blood can stagnate within the left atrial appendage 1966 in an undesirable manner which results in hazardous clotting therein. Blood normally flows to the left atrium 104 through the left pulmonary vein 2170, and if a portion of the inflowing blood could be diverted from the left pulmonary vein through the left atrial appendage 1966, the resultant "flushing" action could keep the blood within the left atrial appendage from stagnating and clotting. Therefore, a flushing conduit 2172 may be used to connect the left pulmonary vein 2170 directly to the left atrial appendage 1966 to facilitate such an alternate flow path.

As shown in FIG. 21, the apparatus 214 has already been used to puncture the walls of the left pulmonary vein 2170 and the left atrial appendage 1966, and the flushing conduit 2172 is depicted as extending therebetween. One of ordinary skill in the art can readily determine the insertion points, direction/order of puncture of the left pulmonary vein 2170 and the left atrial appendage 1966 walls, and method of placing the flushing conduit 2172 for a particular patient. The apparatus 214 may be especially useful in this fourth example use environment because of the need for extremely precise positioning of the ends of the flushing conduit 2172 to fully flush the left atrial appendage 1966 and substantially eliminate stagnation of blood therein.

FIG. 22 depicts a fifth example use environment, including a portion of the abdominal aorta 2274 and the associated common iliac artery 2276, through which the framing member 220 is depicted as extending. The catheter 216 has been inserted in a brachial insertion direction 2278, routed through the abdominal aorta 2274, and the apparatus is now ready to guide a needle (not shown) to puncture the common iliac artery 2276 outward, in a direction such as that indicated by Arrow A (possibly toward the abdominal wall), in the depicted configuration. In this manner, the common iliac artery 2276 can be punctured precisely at a desired target site, avoiding surrounding vascular, neurological, or other structure, and the apparatus 214 can then be used to extend through the abdominal wall and outside the patient's body. Alternately, the target site could be marked or otherwise used to advantage without being punctured or altered. Once the apparatus 214 has exited the body, in a puncture procedure, a sheath or conduit can be extended through the exit point and back to the target site on the common iliac artery 2276. Because of this inside-out access procedure, the user may enter the common iliac artery 2276 at a specific location without fear of piercing all the way through opposing wall of the common iliac artery and "missing" the lumen thereof while damaging the opposing wall. Access in this manner may be desirable, for example, in conducting a percutaneous aortic valve replacement procedure, or any other procedure in which direct access between the common iliac artery 2276 and the outside of the patient's body is desired.

Though not all are depicted in FIG. 22, the framing member 220 could reach the target site shown along any of several paths. For example, the apparatus 214 could be inserted from a corresponding femoral artery (not shown) and advanced toward the depicted target site in a femoral insertion direction 2280. Similarly, and as another example, the apparatus 214 could be inserted from a contralateral femoral artery (not shown) and advanced toward the depicted target site in a contralateral femoral insertion direction 2282. More generally, the fifth example use environment depicted in FIG. 22 is merely one of a multitude of locations within a patient's body where a blood vessel, or other first body cavity or lumen, can be placed into communication with the outside of the patient's body or with at least one other body cavity, whether or not the first body cavity is adjacent the second or more body cavities. For example, the fifth example use environment could be related to an inside-out or outside-in procedure using a carotid or subclavian structure. Indeed, even if no puncture is carried out, the apparatus 214 could be useful in locating a target site in any portion of a patient's vasculature. For example, the target site could be a void, such as a junction point with a side branch or anastomosis location, in a wall of a blood vessel.

In FIG. 23, a sixth example use environment of the present invention is depicted. A blood vessel 2384 is substantially blocked by an obstruction 2386, which may be a blood clot, plaque, or any other obstructive material. The blood vessel 2384 could be any suitable blood vessel 2384 such as, but not limited to, the superficial femoral artery. In order to bypass or remove the obstruction 2386, it may be desirable to route a catheter 216 through the subintimal space 2388 defined within the vessel wall 2390 adjacent the obstruction. As shown in FIG. 23, the catheter 216 has already been guided from the blood vessel lumen 2392 into the subintimal space 2388, optionally through use of the framing member 220 and associated target point 228. The apparatus 214, or portions thereof, are shown as being routed through the subintimal space 2388 in a bypass direction 2394, traveling in parallel with the blood vessel lumen 2392 while avoiding the obstruction 2386. Once the apparatus 214 has passed beyond the obstruction 2386, the framing member 220 and target point 228 can be used to help re-introduce the apparatus to the blood vessel lumen 2392, possibly in the direction of Arrow A. This will establish an alternate or bypass route, through the subintimal space 2388 of the blood vessel 2384, which avoids the obstruction 2386. Since the subintimal space 2388 is very small, an apparatus 214 according to the present invention may be useful in ensuring that the vessel wall 2390 is punctured precisely at the desired location and that the puncture needle (not shown) does not penetrate entirely through the subintimal space and beyond the vessel wall 2390. As with any of the embodiments and example use environments of the present invention, the apparatus 214 can assist with precisely locating the desired target site and, as appropriate, stabilizing the puncture needle to facilitate providing access through a body tissue in a desired manner.

Though cardiovascular applications and environments of the apparatus 214 are given as examples above, it is contemplated that the present invention may be used in any medical application (for example, insertion through the mouth/esophagus and puncturing from the stomach to the peritoneal cavity), or even nonmedical applications (for example, insertion through an electrical conduit and puncturing from the conduit into an adjacent space between wall studs), as appropriate; any procedure requiring relatively precise location of a target site could be a suitable environment for use of the present invention. For example, body cavities with which the apparatus 214 can be used include, but are not limited to, at least one of a left atrium, a right atrium, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, a space external to the patient's body, and the like. Similarly, the body tissue may be, but is not limited to, at least one of an interatrial septum, a left atrial appendage wall, a right atrial appendage wall, a left pulmonary vein wall, a chest wall, an abdominal wall, a heart wall, a blood vessel wall, a common iliac artery wall, a gastrointestinal organ wall, a genitourinary organ wall, a skin of the patient, and the like. Indeed, a puncture need not always be the end result of using the present invention—the apparatus 214 could be applied instead, as discussed throughout, to simply precisely locate (and optionally mark) a specific area within a difficult-to-access structure.

It is also contemplated that, though the apparatus 214 is described as extending, in some example use environments, from an internal body location all the way outside the patient's body, a second catheter, guidewire, trocar, stent, or the like (not shown) could be used to enter the patient's body from externally in any manner, and at least a portion of the apparatus 214 could be linked with that second catheter, guidewire, trocar, stent, or the like inside the patient's body. In this manner, the apparatus 214 can assist in placing the internal body location in communication with an external structure, while the apparatus 214, or portions thereof, does not actually exit the patient's body.

While aspects of the present invention have been particularly shown and described with reference to the preferred embodiment above, it will be understood by those of ordinary skill in the art that various additional embodiments may be contemplated without departing from the spirit and scope of the present invention. For example, the framing member 220, or the framing strands 652 thereof, may have any suitable shape, cross-sectional or otherwise (e.g., the framing member could have a generally tubular aspect provided by loops of framing strands or could resemble a conventional stent). The framing member 220, or the framing strands 652 thereof, may self-expand through the use of memory alloy materials, magnetic attraction/repulsion, or any other desired mechanism. The functions of the framing strands 652 and target wires 230 may be combined in a single structure. A wireless system may selectively provide an electrical signal to the target points 228 similarly to the target wire 230 system. Any number of target points 228 in a target grid 656 may have associated target wires 230. One or more framing members 220 may have a protrusion 224 adapted to enter the superior vena cava 106 or another defined body structure and thereby help position the apparatus 214 in a desired orientation. The framing cross members 654e may be self-expanding and be restrained by the framing strands 652e. The plurality of target points 228 need not be matched in shape, size, attachment method, conductivity, or any other property. The catheter 216 may follow the framing member 220 through the body tissue, or the catheter 216 may remain within the first body cavity. The framing member 220 may extend through a series of body cavities after facilitating punctures through multiple body tissues. Only one apparatus 214 is shown as being present in the embodiments described and shown herein, but any number of apparatus 214 may be used at a time, as desired for a particular application of the present invention. The apparatus 213 could assist in puncturing outward from a first body cavity to a second body cavity, and then successively inward to the first body cavity again. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, I claim:

1. An apparatus for targeting a desired target site on a body tissue that separates a first body cavity from a second body cavity of a patient, the apparatus comprising:
  a catheter having a longitudinally extending catheter lumen and adapted to provide access to the first body cavity;
  a framing member having a collapsed condition in which the framing member is adapted for insertion into the first body cavity through the catheter lumen and an expanded condition in which the framing member is adapted for placement within the first body cavity, the framing member having a framing member body;
  at least one target point carried by the framing member and adapted for placement adjacent the desired target site; and
  at least one target wire attached to at least one target point, at least a portion of the target wire extending through the catheter lumen, and the target wire being substantially spaced apart from the framing member body.

2. The apparatus of claim 1, wherein a plurality of target points are arranged in a target grid carried by the framing member.

3. The apparatus of claim 1, wherein the target wire extends between an external power source and the target point and selectively provides at least one of an electrical and a mechanical signal to the target point to indicate a position of the target point relative to the body tissue in cooperation with an external imaging system.

4. The apparatus of claim 1, wherein the framing member includes at least one framing strand and the first body cavity has an interior first body cavity surface including a portion of the body tissue, the framing strand being adapted to exert positive pressure at a plurality of locations on the interior first body cavity surface to maintain a position of the at least one target point adjacent the body tissue.

5. The apparatus of claim 1, including a puncture needle adapted for insertion through the catheter lumen and into the first body cavity, the puncture needle having a first needle end operative to puncture the body tissue at the target site.

6. The apparatus of claim 1, including a puncture needle connectable to the target wire and adapted for insertion through the catheter lumen and into the first body cavity, the puncture needle having a first needle end operative to puncture the body tissue responsive to guidance by the target wire.

7. The apparatus of claim 1, wherein at least one target point has an associated radiopaque marker to indicate a position of the target point relative to the body tissue in cooperation with an external imaging system.

8. The apparatus of claim 1, wherein each of the first and second body cavities is at least one of a left atrium, a right atrium, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, and a space external to the patient's body.

9. The apparatus of claim 1, wherein the body tissue is at least one of an interatrial septum, a left atrial appendage wall, a right atrial appendage wall, a left pulmonary vein wall, a chest wall, an abdominal wall, a heart wall, a blood vessel wall, a common iliac artery wall, a gastrointestinal organ wall, a genitourinary organ wall, and a skin of the patient.

10. The apparatus of claim 1, wherein the target site is a void in the body tissue.

11. A method for puncturing a body tissue of a patient at a desired target site, the method comprising the steps of:
   inserting a catheter having a longitudinally extending catheter lumen into the patient;
   advancing the catheter into a first body cavity of the patient;
   providing a framing member having a framing member body and carrying at least one target point, the target point adapted for placement adjacent the body tissue to indicate the desired target site;
   providing at least one target wire attached to at least one target point, at least a portion of the target wire extending through the catheter lumen, and the target wire being substantially spaced apart from the framing member body;
   inserting the framing member in a collapsed condition into the first body cavity through the catheter lumen;
   expanding the framing member into an expanded condition within the first body cavity;
   positioning the target point adjacent the desired target site;
   inserting a puncture needle into the first body cavity through the catheter lumen;
   connecting the puncture needle to the target wire;
   guiding the puncture needle to the target point with the target wire; and
   puncturing the body tissue with the puncture needle at the desired target site.

12. The method of claim 11, including the step of adjusting the position of the target point to position the target point adjacent the desired target site.

13. The method of claim 11, including the step of viewing the position of the at least one target point within the first body cavity using an external imaging system.

14. The method of claim 11, wherein the framing member carries a plurality of target points forming a target grid, the method including the steps of:
   positioning the target grid adjacent the body tissue;
   viewing the position of the target grid within the first body cavity using an external imaging system;
   selecting a target point from the target grid, the selected target point being in a predetermined relationship with the desired target site; and
   guiding the puncture needle to the selected target point.

15. The method of claim 11, wherein the first body cavity includes an internal first body cavity surface including a portion of the body tissue, and the step of positioning the target point adjacent the body tissue includes the steps of:
   contacting a plurality of locations on the internal first body cavity surface with the framing member;
   exerting positive pressure at the plurality of locations on the internal first body cavity surface with the framing member; and
   maintaining a position of the target point adjacent the body tissue.

16. The method of claim 11, wherein the framing member is an elongated framing member having longitudinally spaced first and second framing member ends separated by the framing member body, the target point is affixed to the framing member body, the catheter has a catheter outlet end in fluid communication with the first body cavity, and the step of expanding the framing member into a second expanded condition within the first body cavity includes the steps of:
   anchoring the first framing member end adjacent the catheter outlet end;
   advancing the second framing member end toward the first body cavity; and
   bowing the framing member body out into the first body cavity.

17. The method of claim 11, wherein the step of guiding the puncture needle to the target point with the target wire includes the steps of:
   calibrating the target point to have an offset relationship with the desired target site to compensate for an offset distance between the target point and the puncture needle;
   connecting the puncture needle to the target wire; and
   guiding the puncture needle along the target wire to the target point.

18. The method of claim 13, wherein the step of viewing the position of the target point within the first body cavity using an external imaging system includes the steps of:
   selectively providing at least one of an electrical and a mechanical signal through the target wire to the target point;
   providing a visual signal with the target point; and
   viewing the visual signal using the external imaging system.

19. The method of claim 18, wherein the framing member carries a plurality of target points making up a target grid, each target point has a target wire, and the step of viewing the position of the target point within the first body cavity using an external imaging system includes the steps of:
   selectively providing at least one of an electrical and a mechanical signal through a selected target wire to a selected target point;
   providing a visual signal with the selected target point; and
   viewing the visual signal using the external imaging system.

20. The method of claim 11, wherein at least one target point has an associated radiopaque marker to indicate a position of the target point relative to the body tissue in cooperation with an external imaging system.

21. The method of claim 11, wherein each of the first and second body cavities is at least one of a left atrium, a right atrium, a peritoneal cavity, a chest cavity, a left atrial appendage, a right atrial appendage, a left pulmonary vein, a blood vessel, a common iliac artery, a subintimal space, a portion of the heart, a gastrointestinal organ, a genitourinary organ, and a space external to the patient's body.

22. The method of claim 11, wherein the body tissue is at least one of an interatrial septum, a left atrial appendage wall, a right atrial appendage wall, a left pulmonary vein wall, a chest wall, an abdominal wall, a heart wall, a blood vessel wall, a common iliac artery wall, a gastrointestinal organ wall, a genitourinary organ wall, and a skin of the patient.

23. The method of claim 11, wherein the target site is a void in the body tissue.

24. The apparatus of claim 1, wherein the target wire and framing member are not coaxial with one another.

25. The method of claim 11, wherein none of the puncture needle, the target wire, and the framing member are coaxial with one another.

26. The apparatus of claim 1, wherein the at least one target point to which at least one target wire is attached is calibrated to have an offset relationship with the desired target site such that a puncture needle connected to, and offset from, the target wire is guided to the desired target site by the target wire.

* * * * *